(12) United States Patent
Torgerson et al.

(10) Patent No.: US 8,730,032 B2
(45) Date of Patent: May 20, 2014

(54) DETECTION OF PROPER INSERTION OF MEDICAL LEADS INTO A MEDICAL DEVICE

(75) Inventors: Nathan A. Torgerson, Andover, MN (US); James A. Zimmerman, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 262 days.

(21) Appl. No.: 13/265,028

(22) PCT Filed: Apr. 28, 2010

(86) PCT No.: PCT/US2010/032783
§ 371 (c)(1),
(2), (4) Date: Oct. 18, 2011

(87) PCT Pub. No.: WO2010/127014
PCT Pub. Date: Nov. 4, 2010

(65) Prior Publication Data
US 2012/0038477 A1    Feb. 16, 2012

Related U.S. Application Data

(60) Provisional application No. 61/174,188, filed on Apr. 30, 2009.

(51) Int. Cl.
*G08B 1/08*   (2006.01)
*A61B 5/00*   (2006.01)
*G06F 19/00*  (2011.01)

(52) U.S. Cl.
CPC ............. *A61B 5/0031* (2013.01); *A61B 5/0002* (2013.01); *G06F 19/3418* (2013.01)
USPC .................. 340/539.12; 340/539.1; 340/650; 340/657; 600/300

(58) Field of Classification Search
CPC . A61B 5/0002; A61B 5/0031; G06F 19/3418
USPC .......................................... 340/539.1, 539.12
See application file for complete search history.

(56) References Cited

U.S. PATENT DOCUMENTS

| 4,214,804 A | 7/1980 | Little |
| 4,350,169 A | 9/1982 | Dutcher |

(Continued)

FOREIGN PATENT DOCUMENTS

| EP | 0617978 | 10/1994 |
| EP | 1632265 | 3/2006 |

(Continued)

OTHER PUBLICATIONS

PCT/US2010/032783 Search Report and Written Opinion.

*Primary Examiner* — Kerri McNally

(57) ABSTRACT

Proper insertion of medical leads into medical devices is detected at the time the lead is being inserted. An external device initiates impedance testing by the medical device that is receiving the lead prior to the insertion of the lead being completed. The medical device reports back the results of the impedance testing so that the external device can determine whether the lead is properly inserted at the time of lead insertion and can provide an output to a user to indicate whether the lead insertion is proper. The medical device may poll only a last connector expected to be connected before responding, test other connector combinations before or after responding, and so forth.

38 Claims, 5 Drawing Sheets

(56) References Cited

U.S. PATENT DOCUMENTS

| | | | |
|---|---|---|---|
| 4,683,895 A | 8/1987 | Pohndorf | |
| 5,003,992 A | 4/1991 | Holleman et al. | |
| 5,005,587 A | 4/1991 | Scott | |
| 5,473,812 A | 12/1995 | Morris | |
| 5,628,780 A | 5/1997 | Helland | |
| 5,676,659 A | 10/1997 | McGurk | |
| 5,679,022 A * | 10/1997 | Cappa et al. | 439/502 |
| 5,683,444 A | 11/1997 | Huntley | |
| 5,931,861 A | 8/1999 | Werner | |
| 6,141,593 A | 10/2000 | Patag | |
| 6,152,746 A | 11/2000 | Brown | |
| 6,671,554 B2 | 12/2003 | Gibson | |
| 7,187,980 B2 | 3/2007 | Osypka | |
| 2002/0106918 A1 | 8/2002 | Saito et al. | |
| 2002/0111659 A1 | 8/2002 | Davis | |
| 2003/0144718 A1 | 7/2003 | Zeijlemaker | |
| 2005/0137664 A1 | 6/2005 | Sommer | |
| 2005/0222658 A1 | 10/2005 | Hoegh | |
| 2006/0030918 A1 | 2/2006 | Chinn | |
| 2006/0247748 A1 | 11/2006 | Wahlstrand | |
| 2007/0123805 A1 | 5/2007 | Shireman | |
| 2007/0168008 A1 | 7/2007 | Olsen | |
| 2008/0039709 A1 | 2/2008 | Karmarkar | |
| 2008/0183246 A1 * | 7/2008 | Patel et al. | 607/60 |
| 2008/0183263 A1 | 7/2008 | Alexander | |
| 2008/0262582 A1 * | 10/2008 | Alexander et al. | 607/116 |
| 2008/0269863 A1 | 10/2008 | Alexander | |
| 2009/0204192 A1 | 8/2009 | Carlton | |
| 2010/0069743 A1 | 3/2010 | Sheetz | |
| 2012/0035616 A1 | 2/2012 | Olsen | |
| 2012/0035695 A1 | 2/2012 | Olsen | |
| 2012/0035697 A1 | 2/2012 | Stone | |
| 2012/0041528 A1 | 2/2012 | Mehdizadeh | |
| 2012/0041529 A1 | 2/2012 | Olsen | |
| 2012/0046722 A1 | 2/2012 | Olsen | |
| 2012/0130461 A1 | 5/2012 | Olsen | |

FOREIGN PATENT DOCUMENTS

| | | |
|---|---|---|
| EP | 1935449 | 6/2008 |
| GB | 2429154 | 2/2007 |
| WO | WO2007/047966 | 4/2007 |
| WO | WO2008/088568 | 7/2008 |
| WO | WO2008/134196 | 11/2008 |
| WO | WO2008/140376 | 11/2008 |

* cited by examiner

DETECTION OF PROPER INSERTION OF MEDICAL LEADS INTO A MEDICAL DEVICE

RELATED APPLICATIONS

This application is a U.S. National Stage filing under 35 U.S.C. 371 of copending PCT Application No. PCT/US2010/032783, filed Apr. 28, 2010, which claims priority to U.S. Provisional Application 61/174,188, filed on Apr. 30, 2009, the disclosures of each of the above which are incorporated by reference as if re-written herein in their entirety.

TECHNICAL FIELD

Embodiments are related to medical devices and medical leads that are inserted into medical devices to achieve electrical connectivity. More particularly, embodiments relate to detecting whether a medical lead has been properly inserted into a medical device.

BACKGROUND

Medical systems including medical devices that are implantable (IMD) or external and associated implantable medical leads provide functions such as stimulation of muscle or neurological tissue and/or sensing of physiological occurrences within the body of a patient. Typically, the IMD is installed in a subcutaneous location that is accommodating and relatively accessible for implantation. For instance, to provide stimulation near the spine or pelvis, the IMD may be installed in a pocket located on the abdomen or upper buttocks region of the patient. The external device may be located in the same area but outside of the body. The implantable medical lead is installed, either through a percutaneous procedure or a surgical procedure, depending upon the type of lead that is necessary.

Once installed, the lead extends from the stimulation site to the location of the IMD or external device. The separation of the stimulation site to the location of the device varies, but may typically range from about 20 cm to about 100 cm. For relatively lengthy separation, if a lead of adequate length is unavailable then a lead extension may be implanted to span from the device to a proximal end of the implantable lead.

The implantable medical lead includes electrical connectors on a proximal end, electrodes on a distal end, and conductive filars interconnecting the connectors to the electrodes. When an extension is present, the implantable extension includes a connector block on the distal end that connects to the proximal connectors of the lead and includes connectors on the proximal end that connects to the device.

Each connector ring of the proximal end of the lead or extension that is being inserted into the header of the device needs to have a proper electrical connection to an electrical connector within the device. If the electrical connection for each connector of the lead or extension is not proper, then short circuits and/or open circuits may exist between the individual stimulation pathways, where the device may attempt to apply a custom stimulation signal to each simulation pathway during therapy. The short circuits and/or open circuits may adversely affect the stimulation therapy and/or may cause other problems such as reduced battery lifetime due to increased current drain.

Additionally, implantable medical systems are being developed to allow patients having such implantable medical systems to undergo an MRI scan. One manner of doing so may be to include a shield that grounds through a connector that establishes an electrical connection in the header of the device similar to the stimulation connectors. If this ground connector is not properly connected during lead insertion, then the shield may not perform as expected during an MRI scan.

Conventional attempts to verify proper lead insertion involve manually initiating a single lead impedance measurement after the connections have been made. However, waiting until the lead is inserted to manually initiate a impedance test does not provide feedback while the physician is inserting the lead, and the physician is at risk of attempting to insert the lead too far, potentially over-inserting the lead to prevent proper connection, or damaging the lead by kinking the lead due to continued force on the lead after the lead is fully inserted. This lack of feedback can also lead to a trial-and-error technique, where the physician is not sure about the proper insertion and can under insert the lead on the first attempt, which causes additional handling of the device after the measurement is taken in order to re-insert the lead.

SUMMARY

Embodiments address issues such as these and others by detecting whether an implantable medical lead is properly inserted by establishing a communication session between an external device and the medical device prior to completion of the lead insertion. Impedance measurement may begin during the insertion process and feedback can be provided during the insertion procedure.

Embodiments provide a method of verifying that a lead has been fully inserted into a header of a medical device. The method involves prior to completion of the lead being inserted, establishing a communication session between an external device and the medical device. The method further involves during the communication session, instructing the medical device to begin an impedance test for a set of connectors that are expected to be electrically connected to the lead where the impedance test repeatedly polls for impedance. The method further involves receiving a response from the medical device that specifies a result of the impedance testing and providing an output that indicates whether the lead is fully inserted based on the response.

Embodiments provide an external device for verifying that a lead has been fully inserted into a header of a medical device. The external device includes communication circuitry and a processor controlling the communication circuitry. The processor is configured to, prior to completion of the lead being inserted, establish a communication session with the medical device. The processor is further configured to, during the communication session, instruct the medical device to begin an impedance test for a set of connectors that are expected to be electrically connected to the lead where the impedance test repeatedly polls for impedance. The processor is further configured to receive a response from the medical device that specifies a result of the impedance testing and provide an output that indicates whether the lead is fully inserted based on the response.

Embodiments provide a medical device for verifying that a lead has been fully inserted into a header of the medical device. The medical device includes communication circuitry and a processor that controls the communication circuitry. The processor is configured to, prior to completion of the lead being inserted, establish a communication session with an external device. The processor is further configured to, during the communication session, receive an instruction to begin an impedance test for a set of connectors that are expected to be electrically connected to the lead. The processor is further configured to implement the instruction to perform impedance testing where the impedance testing repeatedly polls for impedance and send a response to the external device that specifies a result of the impedance testing.

DETAILED DESCRIPTION

Embodiments provide for detection of whether an implantable medical lead has been properly inserted into a medical device as the lead insertion procedure is occurring. The detection may occur through interaction between an external device and a medical device that the lead is being inserted into. The external device may communicate with the medical device to initiate the detection procedure prior to completion of the lead insertion attempt and the medical device may then report the results back to the external device and/or via audible signaling relatively soon thereafter.

Figure 1:
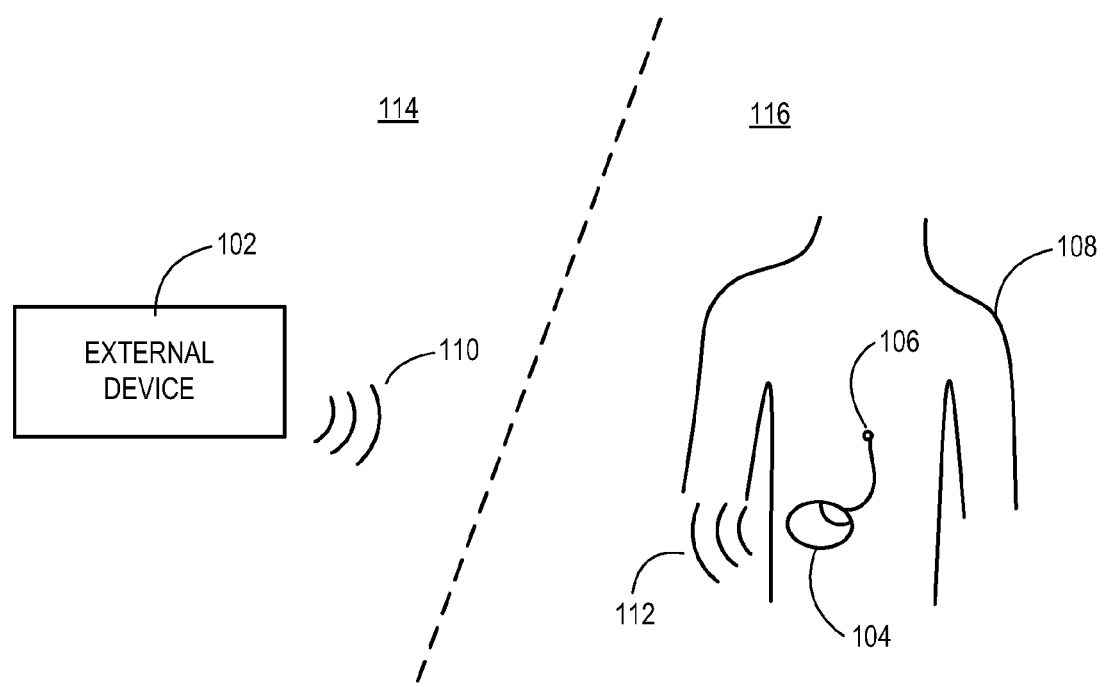
FIG. 1 shows an operating environment for illustrative embodiments that detect whether an implantable medical lead is properly inserted into a medical device.

FIG. 1 shows an external device 102 in communication with a medical device 104 that is affixed to a patient 108 either by being implanted or by an external mounting. The external device 102 may be one of various device types of a device programmer or a dedicated lead insertion detection device. Likewise, the medical device 104 may be of various device types as well such as a stimulator or a monitoring device. The medical device 104 has medical components including implantable medical leads 106 that may be used for stimulation and/or sensing that are being installed in the patient 108 and ultimately connected to the medical device 104. The medical device 104 together with the leads 106 forms a medical system.

The external device 102 and the medical device 104 typically communicate through a form of telemetry. In the case of a wireless communication link, wireless signals 110 are sent by the external device 102 and are received by the medical device 104. Likewise, wireless signals 112 are sent by the medical device 104 and are received by the external device 102. In order to conduct the lead insertion detection procedure, a form of telemetry is used that allows separation between the wireless antenna or head of the external device 102 in an area 114 and the medical device 104 which is in an area 116 where the physician is working. This allows the physician to perform the lead insertion in the area 116 with no telemetry head being an obstruction to the procedure while a communication session between the external device 102 and the medical device 104 is conducted.

As an example, the telemetry may use radio frequency (RF) signaling where an antenna of the external device 102 and the medical device 104 are separated by a larger distance than occurs with near field telemetry to provide added convenience. Another example that may be used is arm's length inductive coupling telemetry where the telemetry head may be separated from the medical device 104 by a distance that prevents the telemetry head from being an obstruction to the lead insertion procedure.

Typically, when the time for detecting that the lead 106 is properly inserted, the external device 102 initiates a communication session with the medical device 104. The external device 102 may instruct the medical device 104 to begin an impedance testing procedure that checks for proper electrical connectivity of the lead 106 to the medical device 104. The medical device 104 then responds with results of the impedance testing to allow the external device 102 to determine if the lead is properly inserted or not and to provide an output that informs a user about the lead insertion.

Figure 2:
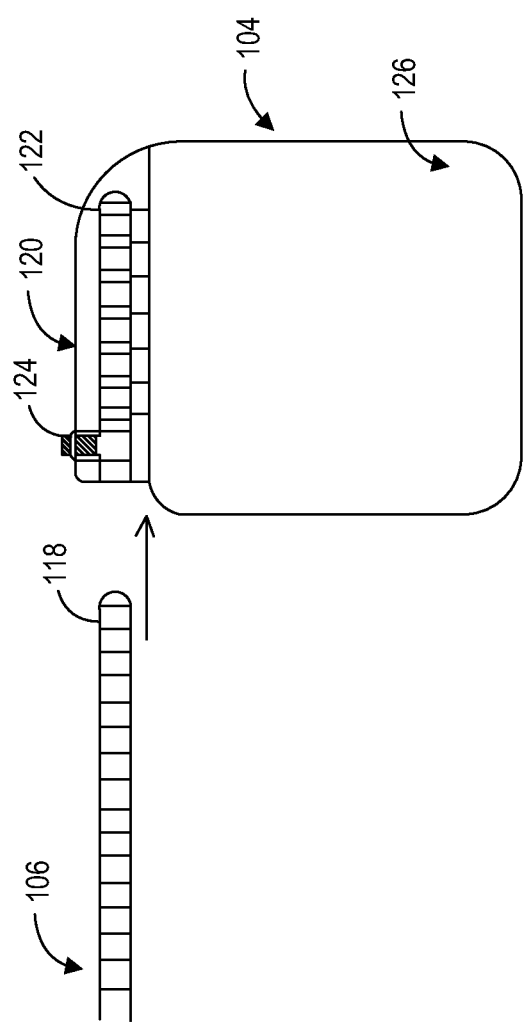
FIG. 2 shows a proximal end of an implantable lead and a header of a medical device that receives the proximal end to complete electrical connections.

FIG. 2 shows a proximal end of the lead 106 as the lead 106 is being inserted into a header 120 of the medical device 104. The header 120 is mounted to a can 126 which encloses the electrical circuitry of the medical device 104. The header 120 includes a passageway that the lead 106 enters to encounter a series of electrical connectors 122. In this particular example, the header 120 includes a set screw block 124 that may be tightened to fix the lead 106 in place once properly inserted.

The end connector 118 of the lead 106 is intended to ultimately connect to an end connector 122 of the header 120. That is an indicator that the lead 106 may be fully inserted. In some cases, the lead 106 may not have an end connector 118 that is far enough on the end to contact the end connector 122 of the header 120 and is instead intended to connect with another connector closer to the set screw block 124. In either case, the medical device 104 may begin first checking the impedance of the connector 122 that is configured to be the last one that will connect with a connector 118 of the lead 106. In this manner, once that impedance indicates a connection, the medical device 104 may then begin a full test of impedance where the many combinations of impedance between connectors can be tested for lead integrity purposes to find impedances that are out of an acceptable range, such as due to short circuits and open circuits, that reveal whether the lead is damaged once the lead is fully inserted.

Figure 3:
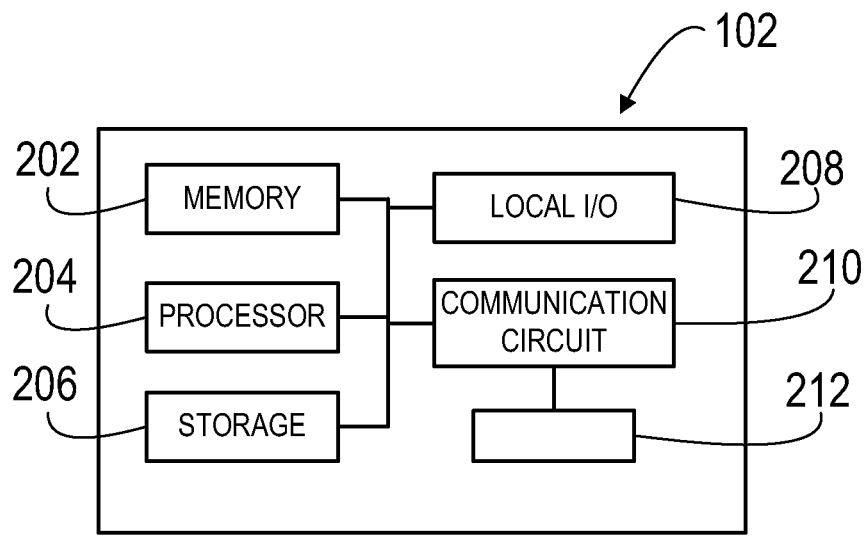
FIG. 3 shows an illustrative external device embodiment that communicates with a medical device to initiate the detection of proper lead insertion.

FIG. 3 shows components of one example of the external device 102. The external device 102 includes a memory 202, a processor 204, and may also include a storage device 206. The external device 102 may also include local input/output (I/O) ports 208 such as to provide local screen displays and to receive user input via a keypad, touchscreen, and so forth. The external device 102 also includes communication circuitry 210 used to establish the telemetry to the medical device 104. The communication circuitry 210 may drive a signal propagation tool 212, such as an RF antenna or an arm's length inductive coupling head.

The memory 202 may be used to store information in use by the processor 204. For instance, the memory 202 may store the results of the impedance testing that has been obtained from the medical device 104. The memory 202 may also store programming that is used by the processor 204 to control the actions of the external device 102 that take place to detect proper lead 106 insertion. The memory 202 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 204 that is implemented to control the verification actions. Examples of the storage device 206 include electronic, magnetic, and optical drives. The storage device 206 and the memory 202 are both examples of computer readable media that may store information in the form of computer programming, data structures, and the like.

Figure 5:
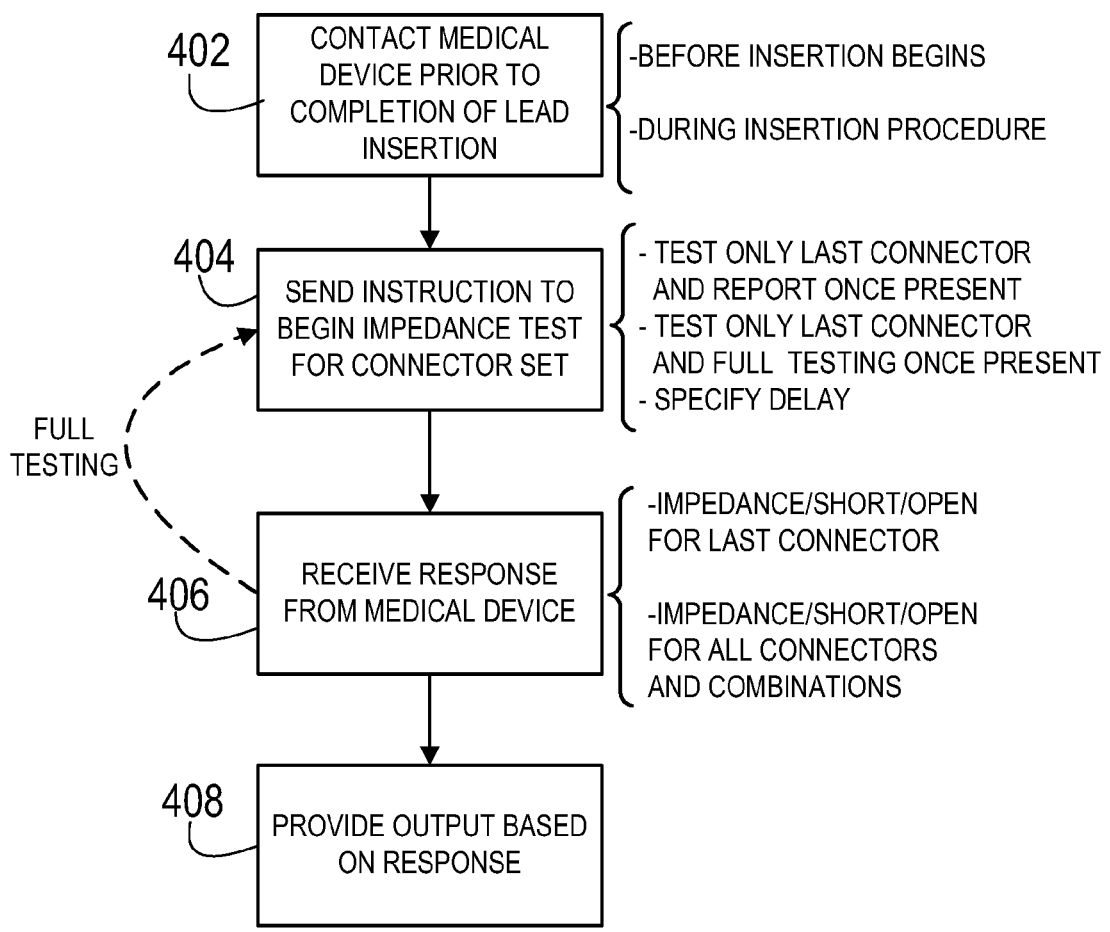
FIG. 5 shows an example of operational flow of external device embodiments that communicate with a medical device to detect proper lead insertion.

The processor 204 performs logical operations such as those of FIG. 5 to allow the external device 102 to communicate with the medical device 104 to initiate the detection of proper lead insertion and to obtain results form the medical device 104. The processor 204 may perform additional logical operations to provide an output of information such as a visual display of impedance testing results including where short circuits or open circuits may be present and an indication of whether the lead 106 is properly inserted. The processor 204 may be of various forms. For instance, the processor 204 may be a general-purpose programmable processor that executes software that is stored on the storage device 208 or elsewhere. Other examples include a dedicated purpose hardware circuit or hard-wired digital logic. The processor 204 may communicate with the various other components through one or more data buses.

Figure 4:
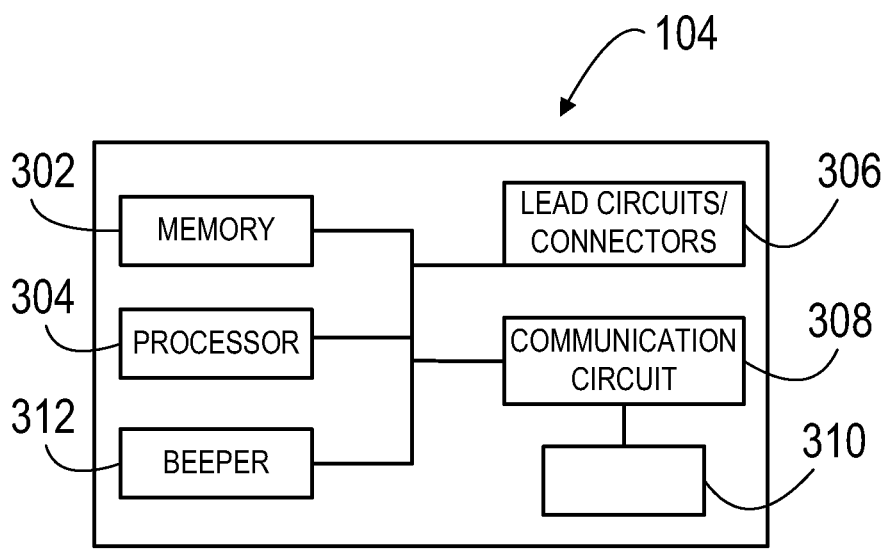
FIG. 4 shows an illustrative medical device embodiment that communicates with an external device to detect proper lead insertion.

FIG. 4 shows components of one example of the medical device 104. The medical device 104 includes a memory 302 and a processor 304. The medical device 104 also includes lead circuitry 306 and the related conductors in the header. The lead circuitry 306 performs medical tasks such as stimulation and/or monitoring but also performs the impedance tests for the various combinations of lead connectors during the detection of proper lead insertion. The medical device 104 also includes communication circuitry 308 used to establish the telemetry to the external device 102. The communication circuitry 308 may drive a signal propagation tool 310, such as an integral RF antenna or an integrated arm's length inductive coupling head.

The lead may also include a transducer 312 such as a piezoelectric beeper that makes a tone as a result of the impedance testing. There could be one tone assigned to when the lead is properly inserted due to an impedance being found for the last connector. There could be another tone that states that the impedances of all connections are within proper ranges, indicating that the device is ready for implant. As the impedance monitoring may continue for a set time beyond the lead insertion, for example 30 minutes, the lead connections may continue to be monitored while the device 104 is being implanted, to ensure that the connections are still good after the implant procedure, and the beeper 312 may sound if the lead is detected to be shorted or open.

The memory 302 may be used to store information in use by the processor 304 such as programming and data values including the impedance testing information. The memory 302 may store additional information including therapy parameters that are used to control the therapy circuitry 306. The memory 302 may be of various types such as volatile, non-volatile, or a combination of the two. The memory 302 is also an example of computer readable media that may store information in the form of computer programming, data structures, and the like.

The processor 304 performs logical operations to allow communication sessions with the external device 102 to occur in order to initiate the procedure for detecting proper lead insertion and to report results back to the external device 102. These logical operations may involve receiving an instruction by the external device 102 to begin impedance testing, either for all connectors or for a last one that is expected to have electrical connectivity to the lead 106.

The processor 304 may also perform other operations requested by the external device 102 or that occur automatically as a result of the request to perform impedance testing. Examples include polling only the last connector expected to electrically connect to the lead until electrical connectivity is detected and then polling all connections or reporting the result of detecting the one connection. Other examples include delaying responding to the external device 102 until a set time has expired or until a particular circumstance is detected such as a given combination of connectors being electrically connected to the lead 106. The processor 304 may be of various forms like those discussed above for the processor 204 of the external device 102. The processor 304 may communicate with the various other components through one or more data buses.

FIG. 5 shows one example of logical operations that may be performed by embodiments of the external device 102 when initiating the detection of proper lead insertion. Initially, the external device 102 contacts the medical device 104 via wireless telemetry to establish a communication session between the two prior to the completion of the lead insertion procedure at a contact operation 402. This communication session may be established while the lead insertion procedure is taking place or before the lead insertion procedure has begun.

Upon establishing the communication session, the external device 102 then sends an instruction to the medical device 104 to instruct the medical device 104 to begin impedance testing for a particular connector set at an instruction operation 404.

This instruction may have several variations. In one embodiment, the instruction may simply be to begin impedance testing where the medical device 104 is already pre-programmed with a procedure to follow. In another embodiment, the instruction may specify a particular procedure that the medical device 104 should follow.

For instance, the instruction may indicate that the medical device 104 should poll for impedance on only the last connector that is expected to achieve electrical connectivity to the lead 106 and then report back about that polling. The instruction may specify to report back periodically regardless of the result or report back only upon the result falling within an impedance range that indicates a connection has been made. The instruction may instead indicate that the medical device 104 should poll for impedance on only the last connector that is expected to achieve electrical connectivity to the lead 106 and once an impedance is detected that indicates that the last connector has connectivity to the lead 106 exists, then begin impedance testing of all connector combinations prior to reporting back the results. The instruction may specify that the medical device 104 should report back after a delay period and/or delay reporting back until significant impedance testing data has been achieved.

In some embodiments where the impedance testing triggered by the operations of FIG. 4 begins before or during lead insertion by testing all connector combinations, it may be beneficial to provide an ongoing indication of lead insertion progress. As the lead is partially inserted, a particular connector within the header will make contact with the most proximal connector of the lead. Thus, from impedance testing all of the connectors of the header, it can be determined which connector(s) within the header make electrical contact with the lead at a given point in time. Thus, the connector deepest within the header that has electrical contact to a connector of the lead 106 represents the progress of the lead insertion where this progress may be reported to the external device 102 and ultimately to the user and clinician. As with other examples, the testing may continue until a polling timeout is reached, until the user manually ends the testing, or until an impedance measurement indicating that the lead 106 is fully inserted is obtained.

Upon sending the instruction, the external device 102 may then listen for a response from the medical device 104 that includes the impedance testing data until receiving the response at a receiving operation 406. The result provided in the response may be an impedance value for the last connection and/or an indication of a short or open circuit, for the last connector. Where the result is solely about the last connector, such as because the instruction to the medical device 104 was to poll only the last connector and then report the results, then the external device 102 may send a subsequent instruction back at the instruction operation 404.

For instance, if the result is an open circuit for the last connector, then the external device 102 may instruct that the medical device 104 continue to poll the last connector again because the lead 106 may not be fully inserted such that the last connector may not yet have connectivity to the lead 106. If the result is a normal impedance, such as 300 ohms to 4,000 ohms, indicating connectivity of the last connector, then the external device 102 may submit an instruction to begin impedance testing all combinations of connectors and to report once that is completed.

The external device 102 may then provide an output to a user that indicates a status of the lead insertion based on the response received from the medical device 104 at an output operation 408. The output may be visual or audible to provide an indication.

For instance, if a response is received that indicates that the last connector is an open circuit, then the output may be that the lead 106 is not properly inserted. If the physician is working with the lead 106 to insert the lead 106 at the time of this indication, then the user may not act on it. However, if the physician appears to have completed the lead insertion and this indication occurs, the user may wish to inform the physician that the lead 106 may not be properly inserted and that further efforts to fully insert it may be necessary.

As another example, if a response is received that indicates that the last connector has a normal impedance, then the output may indicate that proper lead insertion is likely and that a confirmation will be provided after the conclusion of ongoing testing. The user may inform the physician that the lead 106 appears to be properly inserted but that more impedance testing is being done to confirm that conclusion. If a response is received that indicates that any of the connections have a short circuit, then the user may inform the physician that something is abnormal about the lead insertion, either because there is a problem with the lead 106 or with the position of the lead 106 within the header 120.

The logical operations of FIG. 5 may repeat even after proper lead insertion is confirmed. For instance, these logical operations may continue to instruct the medical device 104 to perform the impedance testing after completion of lead insertion and during device implantation to ensure that short circuits and/or open circuits do not develop during the device implantation. The external device 102 may continue to receive the response from the medical device 104 that indicates the result of the impedance testing at the response operation 406 and then provide the corresponding output to the user at the output operation 408.

Figure 6:
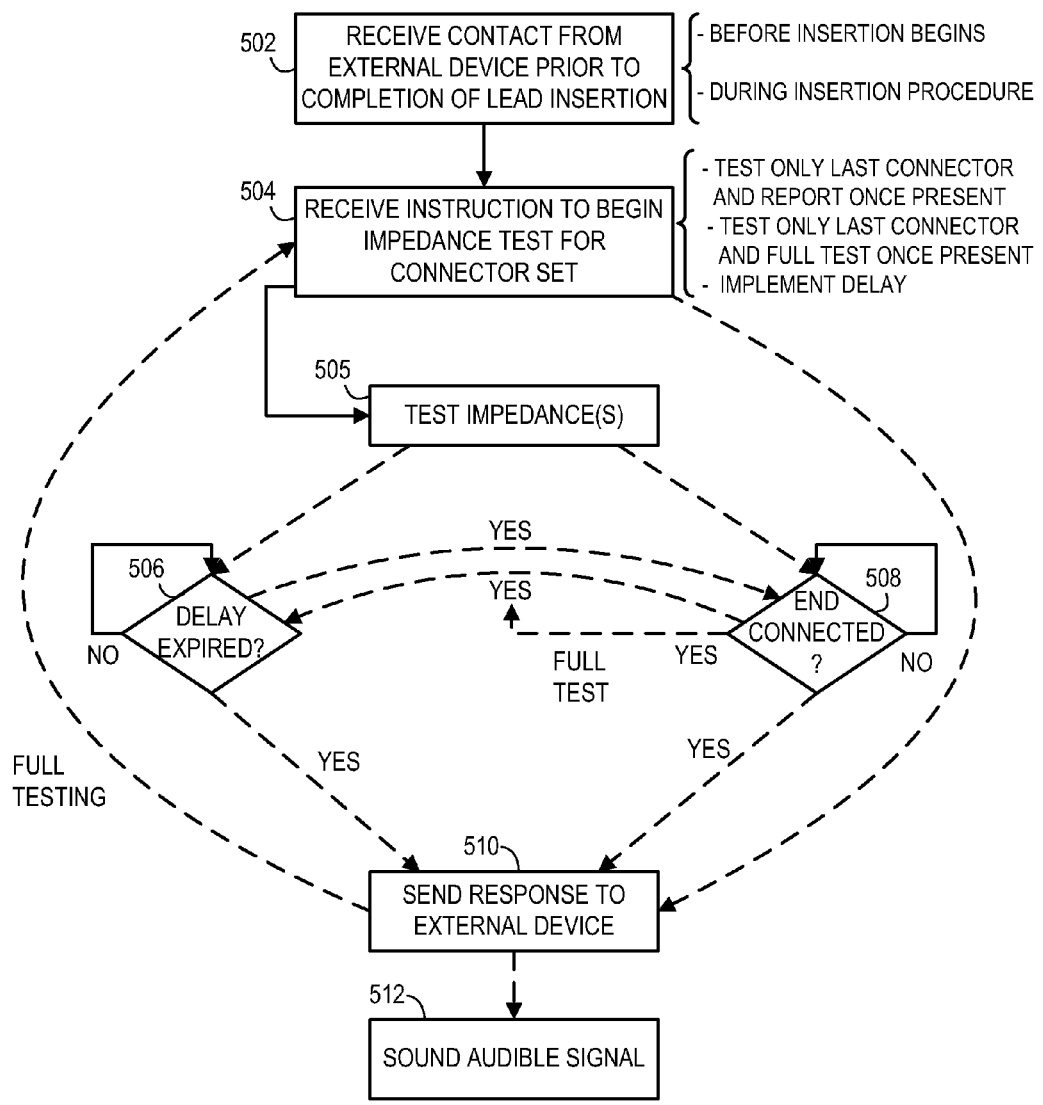
FIG. 6 shows an example of operational flow of medical device embodiments that communicate with an external device to detect proper lead insertion.

FIG. 6 shows an example of an operational flow that may be performed by embodiments of the medical device 104 during the detection of proper lead insertion. These logical operations are complementary to those discussed above in reference to FIG. 5. Initially, the medical device 104 receives contact from the external device 102 via wireless telemetry to establish a communication session between the two prior to the completion of the lead insertion procedure at a contact operation 502. This communication session may be established while the lead insertion procedure is taking place or before the lead insertion procedure has begun.

Upon establishing the communication session, the medical device 104 then receives an instruction from the external device 102 to instruct the medical device 104 to begin impedance testing for a particular connector set at an instruction operation 504. As described above in relation to FIG. 5, this instruction or pre-programmed procedure may have several variations. In one embodiment, the instruction may simply be to begin impedance testing where the medical device 104 is already pre-programmed with a procedure to follow. In another embodiment, the instruction may specify a particular procedure that the medical device 104 should follow. Such procedures are discussed above in relation to the instruction operation 404 of FIG. 5.

Upon receiving the instruction, the medical device 104 may then begin to test the impedance or impedances of interest at testing operation 505. Where the instruction or pre-programmed procedure has been to first poll only the last connector that is expected to have electrical connectivity to the lead 106, then only the impedance of that last connector is tested. Where the instruction is to test some or all connector combinations, then impedances are tested across some or all of the combinations of connectors.

During or after the impedance testing, the medical device 104 may take different approaches depending upon the instruction or the pre-programmed procedure. For instance, the medical device 104 may immediately report a result, regardless of whether connectivity has been found on the last or any other connector, by proceeding directly to a response operation 510 where a response is sent to the external device 102. Such immediate reporting for all connectors allows the progress of lead insertion to be reported to the external device 102 as discussed above in relation to FIG. 5. As another approach, the medical device 104 may decide whether an impedance of the last connector is in a range indicative of connectivity to the lead at query operation 508 and if so, may then proceed to the response operation 510, or may proceed with a full battery of testing at testing operation 505, or may proceed to a query operation 506. As another approach, the medical device 104 may decide whether a delay period for responding to the external device 102 has ended at a query operation 506 and if so, may then proceed to the response operation 510 or may proceed to the query operation 508.

The query operation 506 and query operation 508 may be implemented to reduce the amount of communication occurring between the medical device 104 and the external device 102 that may be less beneficial to determining proper lead insertion. Reducing these communications may be of interest in order to reduce the amount of battery power that is consumed by the communications of the process of detecting proper lead insertion.

As discussed above in reference to FIG. 5, the external device 102 may respond in various ways to the response sent by the medical device 104 at the response operation 510. In some cases, the external device 102 may respond by instructing that the medical device 102 continue to poll only the last connector again because the lead 106 may not be fully inserted or to begin impedance testing all combinations of connectors and to report once that is completed. In either case, the medical device 104 receives the instruction at instruction operation 504, proceeds to test impedance(s) as requested at the testing operation 505, and then carries on with the remainder of the operations.

Additionally or alternatively, the medical device 104 may sound an audible signal at a signal operation 512 using the beeper 312 in order to produce a tone that indicates the lead insertion status. One tone may sound to indicate that the lead is fully inserted due to a valid impedance being found for the last connector. Another tone may sound to indicate that all impedance testing has produced valid impedances such that the lead 106 is ready for use. Other tones may sound to indicate a lack of full insertion or an impedance that is out of range. In such a case, the physician is given immediate feedback without relying on the user of the external device 102 to verbally comment on the results being received from the IMD 104.

The logical operations of FIG. 6 may also repeat even after proper lead insertion is confirmed. For instance, these logical operations may continue to perform the impedance testing at the medical device 104 after completion of lead insertion and during device implantation to ensure that short circuits and/or open circuits do not develop during the device implantation. The medical device 104 may continue to send the response that indicates the result of the impedance testing at the response operation 510 as well as sound an audible tone at the signal operation 512 to indicate that an impedance problem has occurred during device implantation.

While embodiments have been particularly shown and described, it will be understood by those skilled in the art that various other changes in the form and details may be made therein without departing from the spirit and scope of the invention.

What is claimed is:

1. A method of verifying that a lead has been fully inserted into a header of a medical device, comprising:
   prior to completion of the lead being inserted, establishing a communication session between an external device and the medical device;
   during the communication session and prior to completion of the lead being inserted, instructing the medical device to begin an impedance test for a set of connectors that are expected to be electrically connected to the lead where the impedance test repeatedly polls for impedance;
   receiving a response from the medical device that specifies a result of the impedance testing; and
   providing an output that indicates whether the lead is fully inserted based on the response.

2. The method of claim 1, wherein the external device communicates with the medical device via a radio frequency (RF) wireless telemetry.

3. The method of claim 1, further comprising implementing the instruction at the medical device by polling an impedance at at least one connector in the header.

4. The method of claim 3, wherein polling an impedance at at least one connector in the header comprises polling the impedance at a plurality of connectors in the header.

5. The method of claim 3, wherein polling the impedance at at least one connector in the header comprises polling the impedance at a connector that is a last one that is expected to be electrically connected to the lead due to the lead being fully inserted.

6. The method of claim 5, further comprising upon detecting an impedance that indicates connectivity to the lead has been established at the connector that is the last one that is expected to be connected due to the lead being fully inserted, then reporting from the medical device to the external device that the last connector has connectivity to the lead.

7. The method of claim 6, further comprising after the reporting by the medical device, sending an instruction from the external device to the medical device to perform impedance testing for all connectors that are expected to have electrical connectivity to the lead.

8. The method of claim 5, further comprising upon detecting an impedance that indicates connectivity to the lead has been established at the connector that is the last one that is expected to be connected due to the lead being fully inserted, then automatically beginning impedance testing for all connectors that are expected to have electrical connectivity to the lead.

9. The method of claim 1, wherein establishing the communication session between the external device and the medical device begins before insertion of the lead begins.

10. The method of claim 1, further comprising implementing the instruction at the medical device by beginning to poll an impedance at at least one connector in the header before insertion of the lead begins.

11. The method of claim 1, wherein the response indicates a value of the impedance measurements.

12. The method of claim 1, wherein the response comprises an audible signal from the medical device.

13. The method of claim 1, wherein the response indicates which electrical connections to the lead have a short circuit and which have an open circuit.

14. The method of claim 1, wherein instructing the medical device to begin an impedance test for the set of connectors that are expected to be electrically connected to the lead comprises instructing the medical device to respond only upon detecting an impedance value at at least one connector of the set that is indicative of an electrical connection to the lead.

15. The method of claim 1, wherein the medical device sends the response to the external device only upon detecting an impedance value of at least one connector of the set that is indicative of an electrical connection to the lead.

16. The method of claim 1, further comprising:
   continuing to perform the impedance testing at the medical device after completion of lead insertion and during device implantation; and
   continuing to receive the response from the medical device that indicates the result of the impedance testing.

17. An external device for verifying that a lead has been fully inserted into a header of a medical device, comprising:
   communication circuitry; and
   a processor controlling the communication circuitry and being configured to:
      prior to completion of the lead being inserted, establish a communication session with the medical device;
      during the communication session and prior to completion of the lead being inserted, instruct the medical device to begin an impedance test for a set of connectors that are expected to be electrically connected to the lead where the impedance test repeatedly polls for impedance;
      receive a response from the medical device that specifies a result of the impedance testing; and
      provide an output that indicates whether the lead is fully inserted based on the response.

18. The external device of claim 17, wherein the communication circuitry utilizes radio frequency (RF) wireless telemetry.

19. The external device of claim 17, wherein the processor sends an instruction to the medical device to perform impedance testing for at least one connector.

20. The external device of claim 19, wherein the processor sends the instruction to the medical device to perform impedance testing for a plurality of connectors.

21. The external device of claim 19, wherein the at least one connector is a last one that is expected to be connected due to the lead being fully inserted and wherein the processor sends an instruction to the medical device to perform impedance testing for all connectors that are expected to have electrical connectivity to the lead upon receiving a response from the medical device that indicates that electrical connectivity is detected at the connector that is the last one that is expected to be connected due to the lead being fully inserted.

22. The external device of claim 17, wherein the processor establishes the communication session with the medical device before insertion of the lead begins.

23. The external device of claim 17, wherein the processor receives the response that indicates a value of the impedance measurements.

24. The external device of claim 17, wherein processor receives the response that indicates which electrical connections to the lead have a short circuit and which have an open circuit.

25. The external device of claim 17, wherein the processor instructing the medical device to begin the impedance test for the set of connectors that are expected to be electrically connected to the lead comprises instructing the medical device to respond only upon detecting an impedance value at at least one connector of the set that is indicative of an electrical connection to the lead.

26. A medical device for verifying that a lead has been fully inserted into a header of the medical device, comprising:
    communication circuitry; and
    a processor that controls the communication circuitry, the processor being configured to:
        prior to completion of the lead being inserted, establish a communication session with an external device;
        during the communication session and prior to completion of the lead being inserted, receive an instruction to begin an impedance test for a set of connectors that are expected to be electrically connected to the lead;
        implement the instruction to perform impedance testing where the impedance testing repeatedly polls for impedance; and
        send a response to the external device that specifies a result of the impedance testing.

27. The medical device of claim 26, wherein the communication circuitry utilizes a radio frequency (RF) wireless telemetry.

28. The medical device of claim 26, wherein the processor implements the instruction at the medical device by polling an impedance at at least one connector in the header.

29. The medical device of claim 28, wherein the processor polls an impedance at at least one connector in the header by polling the impedance at a plurality of connectors in the header.

30. The medical device of claim 28, wherein the processor polls the impedance at at least one connector in the header by polling the impedance at a connector that is a last one that is expected to be electrically connected to the lead due to the lead being fully inserted.

31. The medical device of claim 30, wherein upon detecting an impedance that indicates connectivity to the lead has been established at the connector that is the last one that is expected to be connected due to the lead being fully inserted, the processor then reports to the external device that the last connector has connectivity to the lead.

32. The medical device of claim 30, wherein upon detecting an impedance that indicates connectivity to the lead has been established at the connector that is the last one that is expected to be connected due to the lead being fully inserted, the processor then automatically begins impedance testing for all connectors that are expected to have electrical connectivity to the lead.

33. The medical device of claim 26, wherein the processor establishes the communication session with the external device before insertion of the lead begins.

34. The medical device of claim 26, wherein the processor implements the instruction at the medical device by beginning to poll an impedance at at least one connector in the header before insertion of the lead begins.

35. The medical device of claim 26, wherein the response indicates a value of the impedance measurements.

36. The medical device of claim 26, wherein the response indicates which electrical connections to the lead have a short circuit and which have an open circuit.

37. The medical device of claim 26, wherein the processor receives an instruction from the external device to respond only upon detecting an impedance value at at least one connector of the set that is indicative of an electrical connection to the lead.

38. The medical device of claim 26, wherein the processor sends the response to the external device only upon detecting an impedance value at at least one connector of the set that is indicative of an electrical connection to the lead.

* * * * *